(12) United States Patent
Zhou et al.

(10) Patent No.: US 8,546,512 B2
(45) Date of Patent: Oct. 1, 2013

(54) COPOLYMER CONTAINING FLUORENYLPORPHYRIN-BENZENE, PREPARATION METHOD AND USE THEREOF

(75) Inventors: Mingjie Zhou, Guangdong (CN); Jie Huang, Guangdong (CN); Yijin Liu, Guangdong (CN)

(73) Assignee: Ocean's King Lighting Science & Technology Co., Ltd., Guangdong (CN)

( * ) Notice: Subject to any disclaimer, the term of this patent is extended or adjusted under 35 U.S.C. 154(b) by 0 days.

(21) Appl. No.: 13/582,807

(22) PCT Filed: Mar. 23, 2010

(86) PCT No.: PCT/CN2010/071228
§ 371 (c)(1),
(2), (4) Date: Sep. 5, 2012

(87) PCT Pub. No.: WO2011/116516
PCT Pub. Date: Sep. 29, 2011

(65) Prior Publication Data
US 2012/0329979 A1 Dec. 27, 2012

(51) Int. Cl.
*C08G 8/02* (2006.01)

(52) U.S. Cl.
USPC ............ 528/216; 528/94; 528/117; 528/118; 528/54; 528/62; 526/171; 526/239

(58) Field of Classification Search
USPC ................. 528/216, 94, 117, 118, 54, 62, 64; 526/171, 239
See application file for complete search history.

(56) References Cited

FOREIGN PATENT DOCUMENTS

| CN | 1459127 A | 11/2003 |
|---|---|---|
| CN | 1887033 A | 12/2006 |
| EP | 1 389 626 A1 | 2/2004 |
| JP | 05-247073 | 9/1993 |

OTHER PUBLICATIONS

Li et al., Macromolecules 2006, 39, 456-461.*
International Search Report for corresponding International Application No. PCT/CN2010/071228 mailed Dec. 30, 2010.
Paul-Roth et al., "Selective anodic preparation of 1D or 2D electroactive deposits from 5,15-bis-(9H-fluoren-2-yl)-10,20-diphenyl porphyrins", Journal of Electroanalytical Chemistry, 2007, vol. 606, No. 2, pp. 103-116.
Yang et al., "Synthesis and Photochromic Properties of Ladderized Poly(p-phenylene-alt-9,10-anthrylene)s", Macromolecules, 2006, vol. 39, No. 17, pp. 5696-5704.
Chinese Office Action for corresponding Chinese Application No. 201080061237.0 mailed Jun. 18, 2013.
Li et al., "Porphyrins with Four Monodisperse Oligofluorene Arms as Efficient Red Light-Emitting Materials", J. Am. Chem. Soc., vol. 126, 2004, pp. 3430-3431.

* cited by examiner

*Primary Examiner* — Shane Fang
(74) *Attorney, Agent, or Firm* — Renner, Otto, Boisselle & Sklar, LLP

(57) ABSTRACT

A copolymer containing fluorenylporphyrin-benzene is disclosed, which comprises a copolymer represented by formula (1), in which $R_1$, $R_2$, $R_3$ and $R_4$, which may be identical or different, are $C_1$-$C_{16}$ alkyl, and n is an integer of 1 to 100. The preparation method of said copolymer containing fluorenylporphyrin-benzene and the use thereof in manufacture of solar batteries components, organic field effect transistors, organic electroluminescent components, organic optical storage components, organic non-linear materials or organic laser components are also disclosed.

11 Claims, 4 Drawing Sheets

(1)

(1)

Providing compounds A and B represented by the following formulae, respectively, and dipyrrolylmethane or 1,4-bis(dipyrrolylmethyl)benzene

Conducting a polycondensation/oxidation reaction of compounds A, B with 1,4-bis(dipyrrolylmethyl)benzene in a system containing a catalyst, an oxidant and an organic solvent, to give the compound represented by formula (1); or conducting a polycondensation/oxidation reaction of compounds A, B and dipyrrolylmethane in a system containing a catalyst, an oxidant and an organic solvent, and conducting a bromination reaction of the product, and conducting a Suzuki coupling reaction of the brominated product with 1,4-bis(4,4,5,5-tetramethyl-1,3,2-dioxaborolanyl)benzene, to give the copolymer represented by formula (1)

Figure 2

COPOLYMER CONTAINING FLUORENYLPORPHYRIN-BENZENE, PREPARATION METHOD AND USE THEREOF

This application is a national phase of International Application No. PCT/CN2010/071228 filed Mar. 23, 2010.

FIELD OF THE INVENTION

The present invention belongs to the field of organic materials, and specifically relates to a fluorenylporphyrin-benzene copolymer, the method for preparation thereof and use thereof.

BACKGROUND OF THE INVENTION

The current world-wide economy is mainly based on fossil energy sources, such as coal, petroleum, and natural gas. However, these un-renewable fossil energy sources are running out. Since the beginning of the $21^{st}$ century, the world-wide energy source problem as well as the problems accompanying it, such as the environment pollution and global warming, are emerging and become more and more severe. Solar energy is considered one of the most potential renewable energy sources, due to its advantages such as its wide distribution, great amount, no pollution, cleanliness, safety, and convenient access.

To sufficiently utilize the energy from sunlight irradiation, new materials capable of absorbing sunlight are developed continuously. Among them, inorganic semi-conductive materials have shown broad development and applications, for example in silicon crystal batteries for ground use. However, their applications are limited by their complex manufacturing process and high cost. In order to lower the cost, and expand the application scope, efforts have long been made to seek new alternative semi-conductive materials.

In recent years, organic materials have drawn great attention. For example, since 1992 when N. S. Sariciftci et al. reported the photo-induced electron transfer phenomenon between a conjugated polymer and $C_{60}$, a great deal of research has been conducted on the use of conjugated polymers in polymeric solar cells, and a rapid progress has been made. A solar cell can directly convert the sunlight energy into electric energy, and is an effective means in utilizing solar energy.

Organic solar cells are a new type of solar cells. Comparing with inorganic semi-conductive materials which have disadvantages such as limited sources, high price, toxicity, complex manufacturing process and high cost, organic solar cells have advantages which cannot be compared by inorganic solar cells, such as broad sources of the materials, diversity and controllability of the structures, low cost, safety and environment-friendliness, simple manufacturing process, light weight, capability of being flexibly manufactured in large areas. Therefore, organic solar cells may be widely used in architecture, illumination, and power generation, and have important prospect in development and applications. However, the energy conversion efficiency of organic solar cells so far is much lower than that of the inorganic solar cells. Accordingly, development of new organic materials is important for increasing the efficiency of organic solar cells and other semi-conductive devices or photo-electric devices.

SUMMARY OF THE INVENTION

Accordingly, the present invention provides a fluorenylporphyrin-benzene copolymer with a broad spectral response and good stability, as well as a method for preparing the fluorenylporphyrin-benzene copolymer with a simple procedure and low cost.

An embodiment of the present invention also provides use of the fluorenylporphyrin-benzene copolymer in organic photo-electric materials, solar cell devices, organic field effect transistors, organic electroluminescent devices, organic optical storage devices, organic non-linear materials or organic laser devices.

A fluorenylporphyrin-benzene copolymer is provide, which comprises a copolymer represented by formula (1):

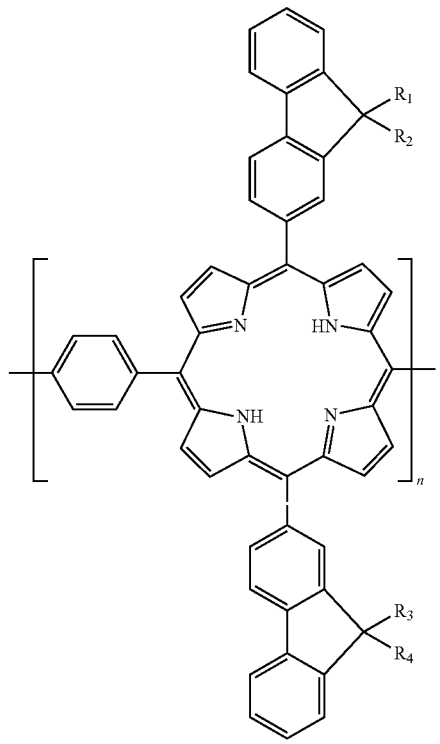

(1)

wherein, $R_1$, $R_2$, $R_3$, $R_4$ are the same or different from each other and are $C_1$-$C_{16}$ alkyl; and n is an integer of 1-100.

Also provided is a method for preparing a fluorenylporphyrin-benzene copolymer, comprising the steps of:

providing compounds A and B represented by the following formulae, respectively, and dipyrrolylmethane or 1,4-bis(dipyrrolylmethyl)benzene,

A:

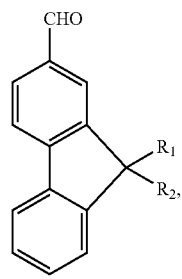

B:

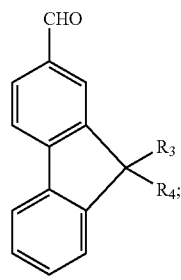

wherein $R_1$, $R_2$, $R_3$, $R_4$ are the same or different from each other and are $C_1$-$C_{16}$ alkyl;

conducting a polycondensation/oxidation reaction of compounds A, B with 1,4-bis(dipyrrolylmethyl)benzene in a system containing a catalyst, an oxidant and an organic solvent, to give the compound represented by formula (1); or conducting a polycondensation/oxidation reaction of compounds A, B with dipyrrolylmethane in a system containing a catalyst, an oxidant and an organic solvent, and conducting a bromination reaction of the product, and conducting a Suzuki coupling reaction of the brominated product with 1,4-bis(4,4,5,5-tetramethyl-1,3,2-dioxaborolanyl)benzene, to give the copolymer represented by formula (1):

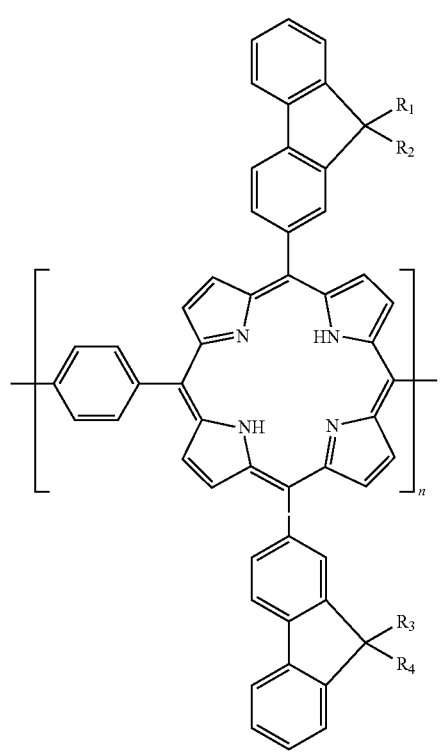

(1)

wherein n in formula (1) is an integer of 1-100.

Further provided is use of the above fluorenylporphyrin-benzene copolymer in organic photo-electric materials, solar cell devices, organic field effect transistors, organic electroluminescent devices, organic optical storage devices, organic non-linear materials or organic laser devices.

In the above fluorenylporphyrin-benzene copolymer, the fluorenyl or derivatives thereof have superior photo- and thermal stabilities and film-forming properties, and its structure is easy to be modified. By introducing a benzene ring into the above copolymer, the electron cloud density of the skeleton of the polymer is increased, thereby making the band gap of the fluorenyl copolymer narrower, and the spectral response range broader. The porphyrin structure makes the copolymer to have higher quantum efficiency in charge transfer and energy transfer, good electron buffering property and optical, electrical and magnetic properties, good stiffness and softness, good thermal stability and environmental stability. When the above fluorenylporphyrin-benzene copolymer is used in organic photo-electric materials, solar cell devices, organic field effect transistors, organic electroluminescent devices, organic optical storage devices, organic non-linear materials or organic laser devices, it can improve their photo-electric or semi-conductor-related properties, and lower the weight of the devices, and facilitate their mass production.

BRIEF DESCRIPTION OF THE DRAWINGS

The present invention will be described in detail by referring to the figures and Examples, in which:

FIG. 2 is a flow chart of a method for preparing a fluorenylporphyrin-benzene copolymer in an embodiment of the present invention;

DETAILED DESCRIPTION OF THE PREFERRED EMBODIMENTS

In order to make the objects, the technical solutions, and the advantageous effects of the present invention more obvious, the present invention will be described in detail by referring to the figures and Examples. It shall be appreciated that the specific embodiments described herein are only for illustration of the present invention and shall not be construed to limit the present invention.

Figure 1:
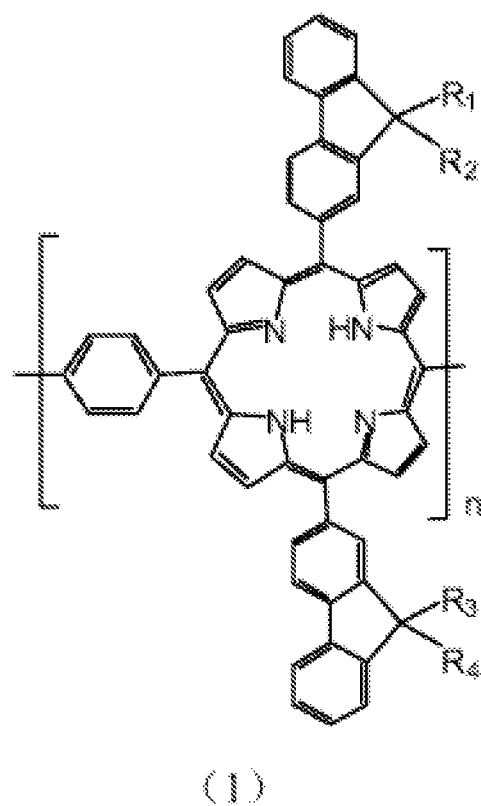
FIG. 1 illustrates the structure of a fluorenylporphyrin-benzene copolymer in an embodiment of the present invention.

Refer to FIG. 1, which shows the structure of a fluorenylporphyrin-benzene copolymer in an embodiment of the present invention, i.e. the copolymer represented by formula (1):

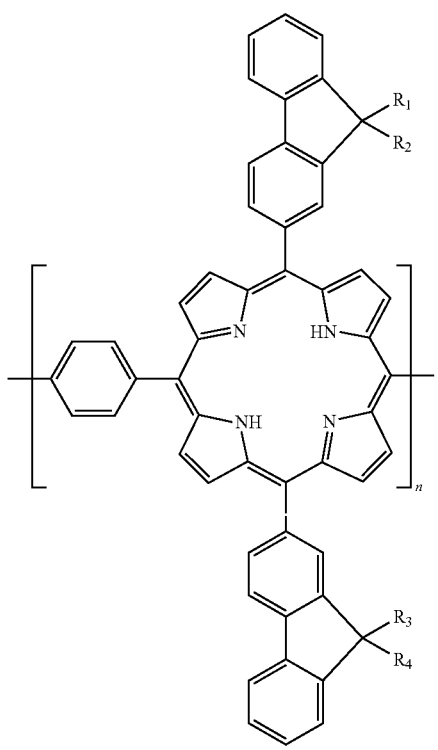

(1)

wherein $R_1$, $R_2$, $R_3$, $R_4$ are the same or different from each other and are $C_1$-$C_{16}$ alkyl; and n is an integer of 1-100.

In an embodiment of the present invention, the two alkyl-containing fluorenyl in each unit of the fluorenylporphyrin-benzene copolymer are the same, i.e. for example, $R_1$, $R_3$ are the same $C_1$-$C_{16}$ alkyl, and $R_2$, $R_4$ are the same $C_1$-$C_{16}$ alkyl; or alternatively, $R_1$, $R_4$ are the same $C_1$-$C_{16}$ alkyl, and $R_2$, $R_3$ are the same $C_1$-$C_{16}$ alkyl. This makes it possible to simplify the preparation process and lower the production cost. Introduction of alkyl at 9-position helps to improve the solubility of the copolymer, facilitates the film-forming processing, and expands its application scope. Preferably, $R_1$, $R_2$, $R_3$, $R_4$ are the same $C_1$-$C_{16}$ alkyl. n is an integer of preferably 5-50, more preferably 10-30. In a specific embodiment of the present invention, $R_1$, $R_2$, $R_3$, $R_4$ are alkyl having six or more carbon atoms.

The fluorenylporphyrin-benzene copolymer comprises fluorenyl or a derivative thereof, a porphyrin structure and a benzene ring structure. Fluorenyl or derivatives thereof have superior photo- and thermal stability and film-forming properties, and its structure is easy to be modified. By introducing a benzene ring into the above copolymer, the electron cloud density of the skeleton of the fluorenylporphyrin-benzene copolymer is increased, thereby making the band gap of the copolymer narrower, and the spectral absorption range broader. The porphyrin structure makes the copolymer to have higher quantum efficiency in charge transfer and energy transfer, good electron buffering property and optical, electrical and magnetic properties, good stiffness and softness, good thermal stability and environmental stability.

Accordingly, the above fluorenylporphyrin-benzene copolymer has broad spectral response, ranging in about 300-700 nm, which substantially encompass the visible light range. In addition, it has good thermal stability and environmental stability, and shows good photoelectric properties. In the fluorenylporphyrin-benzene copolymer of the present embodiment, $R_1$, $R_2$, $R_3$, $R_4$ are preferably alkyl chain, for example alkyl chain having six or more carbon atoms. By introducing alkyl chain, the solubility of the material is improved, which facilitates film-forming processing and expands its application scope.

Referring to FIG. 2, the method for preparing the fluorenylporphyrin-benzene copolymer described above comprises the steps of:

S01: providing compounds A and B represented by the following formulae, respectively, and dipyrrolylmethane or 1,4-bis(dipyrrolylmethyl)benzene,

A:

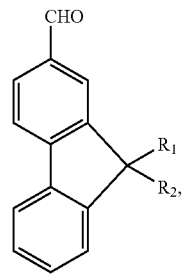

B:

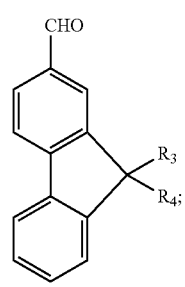

wherein $R_1$, $R_2$, $R_3$, $R_4$ are the same or different from each other and are $C_1$-$C_{16}$ alkyl;

S02: conducting a polycondensation/oxidation reaction of compounds A, B with 1,4-bis(dipyrrolylmethyl)benzene in a system containing a catalyst, an oxidant and an organic solvent, to give the compound represented by formula (1); or conducting a polycondensation/oxidation reaction of compounds A, B with dipyrrolylmethane in a system containing a catalyst, an oxidant and an organic solvent, and conducting a bromination reaction of the product, and conducting a Suzuki coupling reaction of the brominated product with 1,4-bis(4,4,5,5-tetramethyl-1,3,2-dioxaborolanyl)benzene, to give the copolymer represented by formula (1):

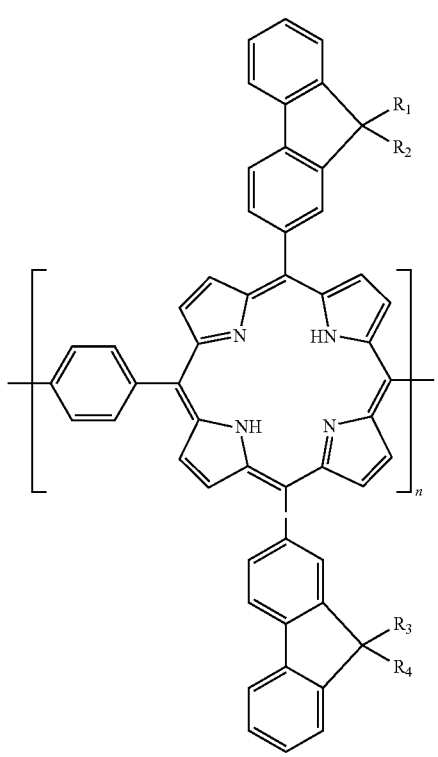

(1)

wherein n in formula (1) is an integer of 1-100.

In step S01, compounds A and B may be commercially available or prepared with available synthesis methods. $R_1$, $R_2$, $R_3$, $R_4$ may be selected in the same way as described above for the fluorenylporphyrin-benzene copolymer, which will not be described repeatedly. For example, as described above, in a preferred embodiment, $R_1$, $R_3$ are the same $C_1$-$C_{16}$ alkyl, and $R_2$, $R_4$ are the same $C_1$-$C_{16}$ alkyl. As compounds A and B have the same structure, one less raw materials are needed, which simplifies the preparation process and lowers the cost, and provides higher yields comparing with the case wherein different compounds A and B are used.

In the present embodiment, compounds A, B and dipyrrolylmethane, 1,4-bis(dipyrrolylmethyl)benzene may be prepared as follows, respectively.

1. Preparation of Compounds A and B

Taking compound A as an example, the preparation thereof comprises the following steps.

Step 1: conducting a substitution reaction of 2-bromofluorene with bromoalkanes in the presence of a catalyst and an organic solvent to give 9,9-dialkyl-2-bromofluorene. The catalyst is tetrabutylammonium bromide or benzyltriethylammonium bromide; and the organic solvent is toluene, dimethyl sulfoxide or tetrahydrofuran. Correspondingly, the bromoalkanes are those in which the alkyls are $R_1$ and $R_2$, respectively. As shown below, the reaction is carried out in two reaction steps, i.e. steps i and ii, wherein the substitution reactions are carried out with two bromoalkanes (when $R_1$ and $R_2$ are the same, the two bromoalkanes are the same), the reaction scheme being shown below:

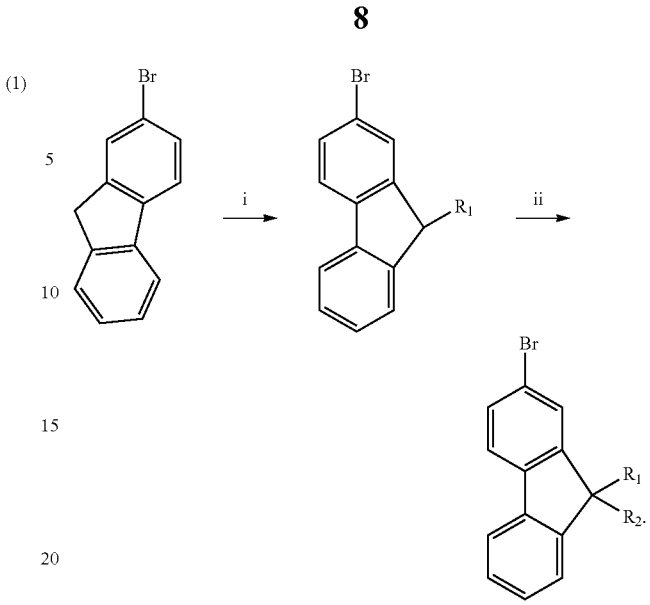

For detailed description of the preparation of 9,9-dialkyl-2-bromofluorene, reference can be made to *Macromolecules*, 2002, 35, 3474.

Step 2: converting bromo to aldehyde group in a system containing alkyl lithium, dimethyl formamide and an organic solvent, the reaction scheme being shown below:

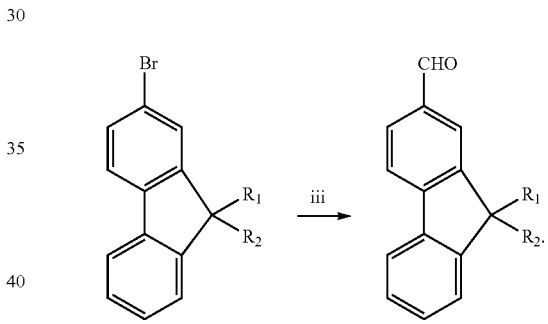

In a specific embodiment, the alkyl lithium is n-butyl lithium; the organic solvent is tetrahydrofuran. For detailed description of the preparation, reference can be made to *Macromolecules*, 2006, 39, 456.

The steps for preparing compound B are the same, except that the alkyls in the two bromoalkanes are $R_3$ and $R_4$, respectively.

2. Preparation of Dipyrrolylmethane

A condensation reaction is conducted in a system containing formaldehyde, a catalyst and pyrrole, to give dipyrrolylmethane, the reaction scheme being shown below:

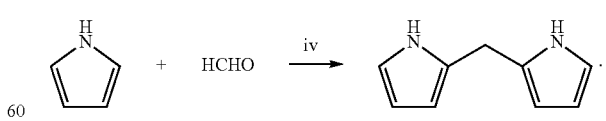

The catalyst for step iv may be trifluoroacetic acid, or boron trifluoride-dimethyl ether complex ($BF_3.(CH_3)_2O$), but is not limited thereto. Pyrrole acts as both the organic solvent and a reactant. For detailed description of the preparation of dipyrrolylmethane, reference can be made to *Tetrahedron*, 1994, 39, 11427.

3. Preparation of 1,4-bis(dipyrrolylmethyl)benzene

A condensation reaction is conducted in a system containing terephthalaldehyde, a catalyst and pyrrole to give 1,4-bis(dipyrrolylmethyl)benzene, the reaction scheme being shown below:

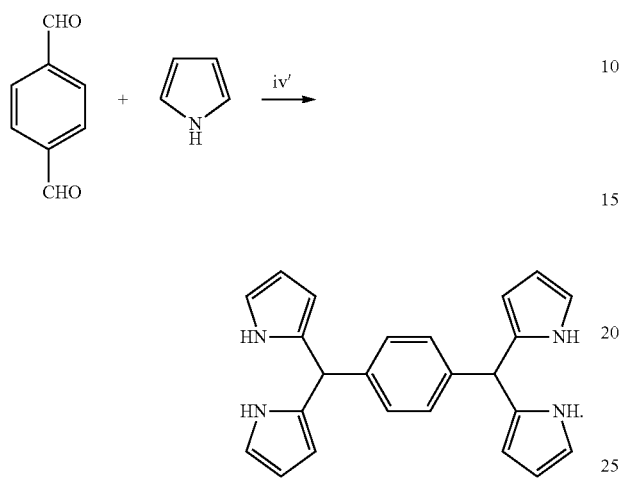

The catalyst for step iv' may be trifluoroacetic acid, or boron trifluoride-dimethyl ether complex ($BF_3 \cdot (CH_3)_2O$), but is not limited thereto. Pyrrole acts as both the organic solvent and a reactant. For detailed description of the preparation of 1,4-bis(dipyrrolylmethyl)benzene, reference can be made to *Tetrahedron*, 1994, 39, 11427.

Step S02 may be carried out in two schemes depending on the two different reactants, dipyrrolylmethane and 1,4-bis(dipyrrolylmethyl)benzene. The first scheme comprises: conducting a polycondensation/oxidation reaction of compounds A, B with 1,4-bis(dipyrrolylmethyl)benzene in a system containing a catalyst, an oxidant and an organic solvent, to give the fluorenylporphyrin-benzene copolymer described above. The second scheme comprises: conducting a polycondensation/oxidation reaction of compounds A, B with dipyrrolylmethane in a system containing a catalyst, an oxidant and an organic solvent, and conducting a bromination reaction of the product, and conducting a Suzuki coupling reaction of the brominated product with 1,4-bis(4,4,5,5-tetramethyl-1,3,2-dioxaborolanyl)benzene, to give the fluorenylporphyrin-benzene copolymer described above. The molar ratio of the reactants may be stoichiometric ratio or other ratios, e.g., some reactants may be in excess. All these ratios may be applicable in carrying out the reactions in the present embodiment, without affecting the process of the reactions. The reactions will be described as follows.

As described above, the first scheme for carrying out step S02 comprises conducting a polycondensation/oxidation reaction of compounds A, B with 1,4-bis(dipyrrolylmethyl)benzene. The catalyst for the polycondensation/oxidation reaction may be trifluoroacetic acid, or the like. The oxidant may be dichloro dicyano benzoquinone (DDQ), or the like, but is not limited thereto. The organic solvent may be dichloromethane, tetrahydrofuran, carbon tetrachloride, chloroform, acetonitrile, or the like. The reaction scheme is shown below:

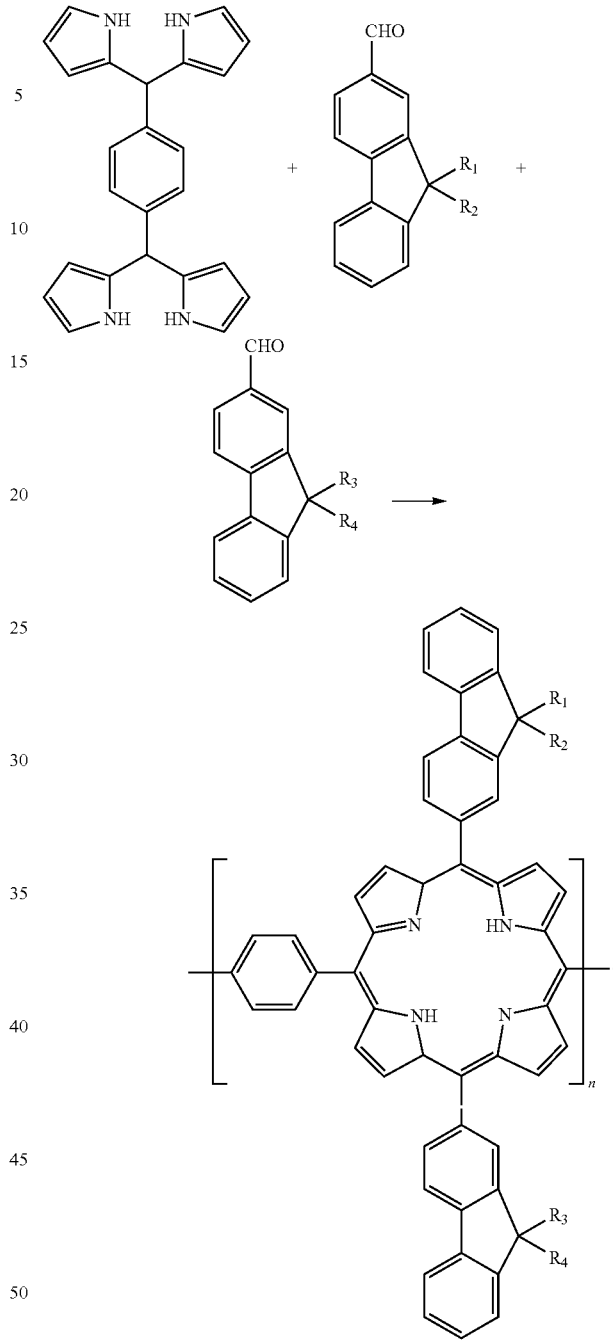

The specific procedure is as follows. A moisture-free and oxygen-free system is set up. Compounds A, B and 1,4-bis(dipyrrolylmethyl)benzene (in a molar ratio of 1/1/1) are weighted into the reaction container, and dissolved in an organic solvent. An appropriate amount of trifluoro acetic acid is added and stirred overnight (e.g. 12-14 hours). Two equivalents (i.e. two times of the stoichiometric amount) of dichloro dicyano benzoquinone are added, and continuously stirred. Triethylamine is added to quench the reaction. Purification is conducted as follows: concentrating, filtering, washing the solid, collecting the filtrate, evaporating half of the solvents, adding methanol, standing for precipitation, filtering, collecting the solid, conducting silica gel column chromatographic separation, drying, to obtain the product, i.e. the fluorenylporphyrin-benzene copolymer described above. The silica gel column chromatographic separation uses petroleum ether/ethyl acetate as the eluent.

The second scheme for carrying out step S02 comprises the following steps:

1) conducting a polycondensation/oxidation reaction of compounds A, B with dipyrrolylmethane in a system containing a catalyst, an oxidant and an organic solvent, to give a fluorenylporphyrin compound. This step 1) is similar to the reaction in the first scheme, and the mechanism thereof is also a polycondensation/oxidation reaction. The difference thereof lies in that the reactant is dipyrrolylmethane, and thereby giving a fluorenylporphyrin compound. Similarly, the catalyst may be trifluoroacetic acid, or the like. The oxidant may be dichloro dicyano benzoquinone (DDQ), or the like, but is not limited thereto. The organic solvent may be dichloromethane, tetrahydrofuran, carbon tetrachloride, chloroform, acetonitrile, or the like. The reaction scheme is shown below:

The specific procedure is as follows. A moisture-free and oxygen-free system is set up. Compounds A, B and dipyrrolylmethane (for example in a molar ratio of 1/1/2) are weighted and dissolved in an organic solvent, and charged with nitrogen. Trifluoro acetic acid is added, followed by adding two equivalents of dichloro dicyano benzoquinone. Stirring is continued. Triethylamine is then added to quench the reaction. Purification is conducted as follows: concentrating by removing the organic solvent, filtering, collecting the filtrate, removing the organic solvent by rotary evaporation, conducting flash silica gel column chromatographic separation eluted with dichloromethane, removing the organic solvent by rotary evaporation, and recrystallizing in ethyl ether/methanol to give the product, i.e. fluorenylporphyrin compound.

2) conducting a bromination reaction of the fluorenylporphyrin compound obtained in step 1) in a system containing a catalyst and an organic solvent, to give a dibromo fluorenylporphyrin compound. Specifically, the catalyst may be, but not limited to, pyridine, a pyridine derivative, or triethylamine. The organic solvent may be, but not limited to, chloroform, tetrahydrofuran, dimethyl formamide (DMF), carbon tetrachloride, dichloromethane or acetonitrile. N-bromosuccinimide (NBS), $Br_2$, HBr, $PBr_3$, or the like, preferably NBS, may be added as a bromine source. The specific procedure is as follows. The fluorenylporphyrin compound (e.g. 5,15-bis(9,9-dialkylfluorenyl)porphyrin) is dissolved in chloroform, followed by added a small amount of pyridine. The reaction mixture is cooled to 0° C., followed by adding an appropriate amount of N-bromosuccinimide. After stirring, the mixture is warmed back to room temperature, and stirred for further several hours. Acetone is added to terminate the reaction. The solvents are removed and the residue is recrystallized in ethyl ether/methanol to give the product. The reaction scheme is shown below:

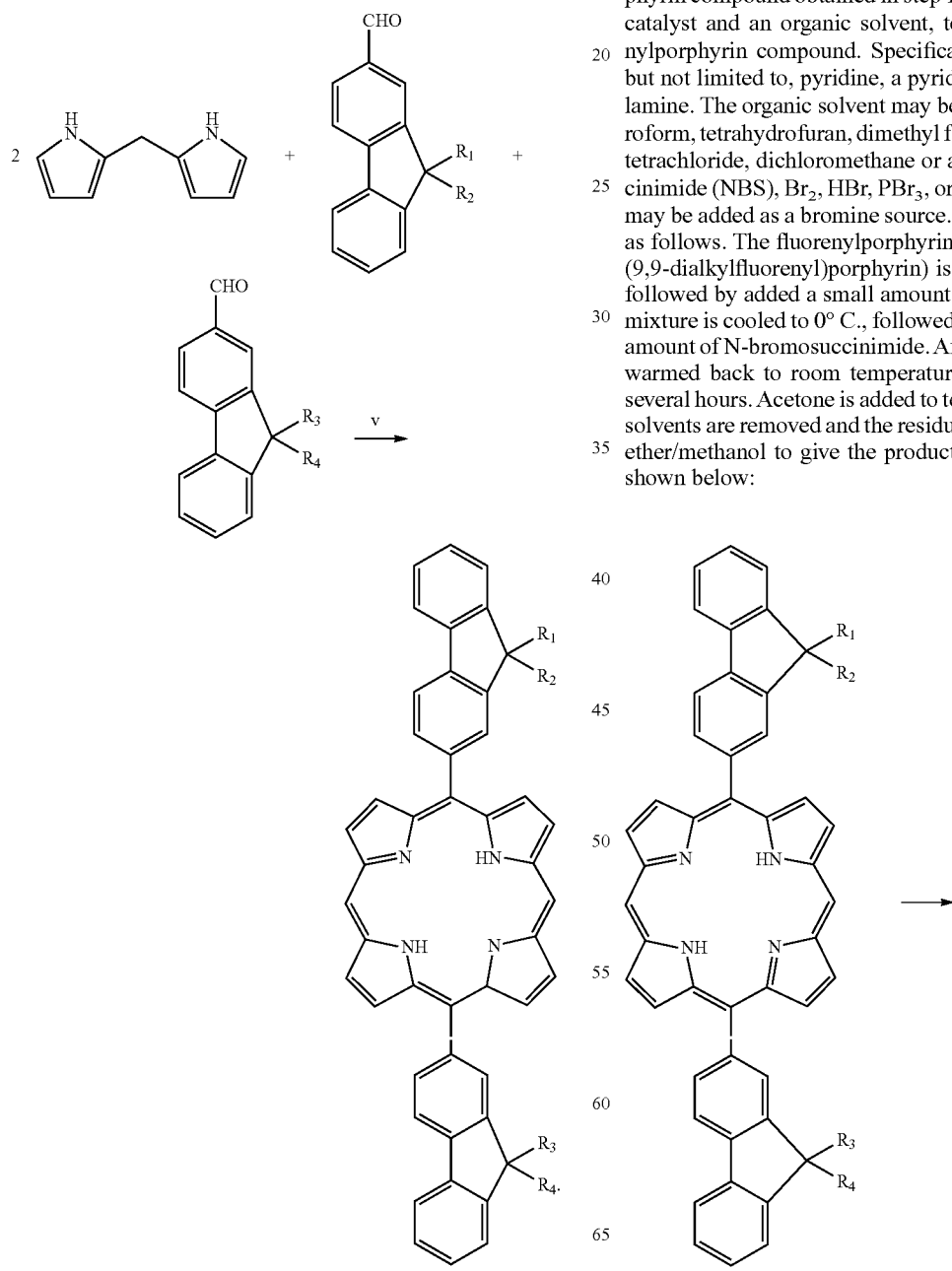

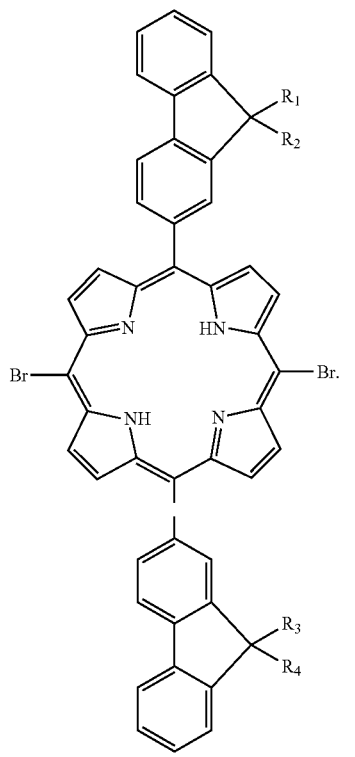

3) conducting a Suzuki coupling reaction of the dibromo fluorenylporphyrin compound with 1,4-bis(4,4,5,5-tetramethyl-1,3,2-dioxaborolanyl)benzene in the presence of a catalyst, an organic solvent and an alkali solution, to give the fluorenylporphyrin-benzene copolymer described above.

The catalyst for step 3) may be an organic palladium catalyst, and the amount thereof may be 0.1-20% of the molar amount of 1,4-bis(4,4,5,5-tetramethyl-1,3,2-dioxaborolanyl) benzene. The organic palladium catalyst may be, but not limited to, $Pd_2(dba)_3/P(o\text{-}Tol)_3$, $Pd(PPh_3)_4$ or $Pd(PPh_3)_2Cl_2$. The organic solvent may be, but not limited to, tetrahydrofuran, dichloromethane, ethylene glycol dimethyl ether, benzene or toluene, preferably toluene. The amount of the organic solvent should be sufficient to dissolve the reactants to make them reacting sufficiently. The alkali solution may be an inorganic alkali solution or an organic alkali solution. The inorganic alkali solution may be an aqueous solution of alkali metal hydroxide or alkali metal carbonate, for example, but not limited to sodium hydroxide solution, potassium hydroxide solution, sodium carbonate solution, potassium carbonate solution, preferably sodium carbonate solution. The organic alkali solution may be an aqueous solution of alkylammonium hydroxide, for example, but not limited to, an aqueous solution of tetramethylammonium hydroxide, tetraethylammonium hydroxide, tetrapropylammonium hydroxide, or tetrabutylammonium hydroxide. The amount of the alkali solution may be 5-20 times of the molar amount of compound D.

In a specific embodiment, 1,4-bis(4,4,5,5-tetramethyl-1,3,2-dioxaborolanyl)benzene may be prepared in advance, for example by the following substitution reaction under the action of butyl lithium and boric acid ester:

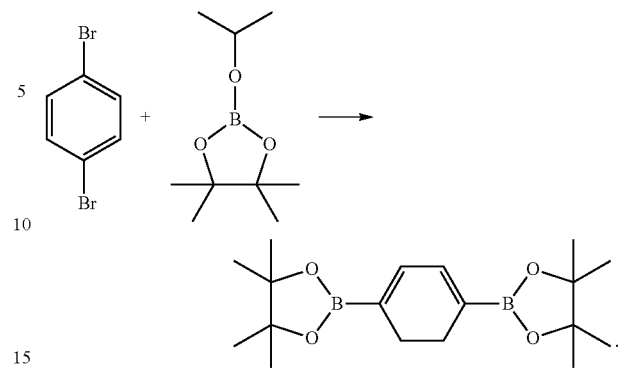

The specific procedure is as follows. Under $N_2$ protection, 1,4-dibromobenzene is added into a three-necked flask. Tetrahydrofuran solvent is added with a syringe. Under −78° C., n-butyl lithium is added slowly with a syringe, and further stirred for several hours. Under −78° C., 2-iso-propyloxy-4,4,5,5-tetramethyl-1,3,2-dioxaborolanyl is added with a syringe. The reaction mixture is stirred at room temperature overnight (about 12-14 hours). Saturated sodium chloride aqueous solution is added to terminate the reaction. The solution is extracted with chloroform, dried over anhydrous sodium sulfate, and filtered. The filtrate is collected, and the solvent is rotary evaporated. The crude product is purified with silica gel chromatography, using petroleum ether/ethyl acetate as the eluent, to give the product.

The reaction between 1,4-bis(4,4,5,5-tetramethyl-1,3,2-dioxaborolanyl)benzene and the dibromo fluorenylporphyrin compound is shown below:

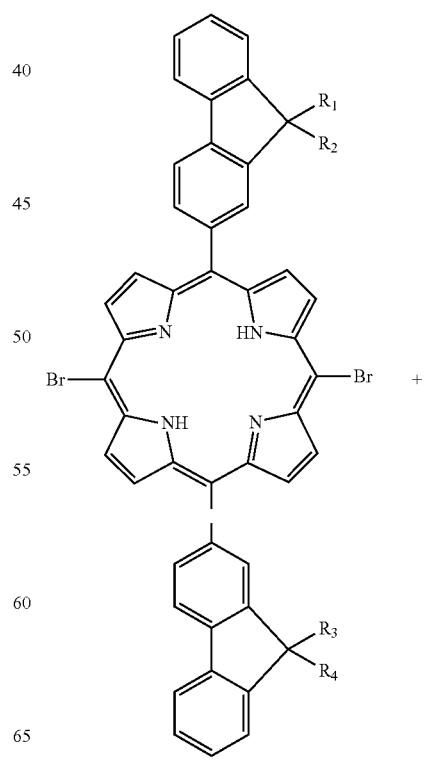

-continued

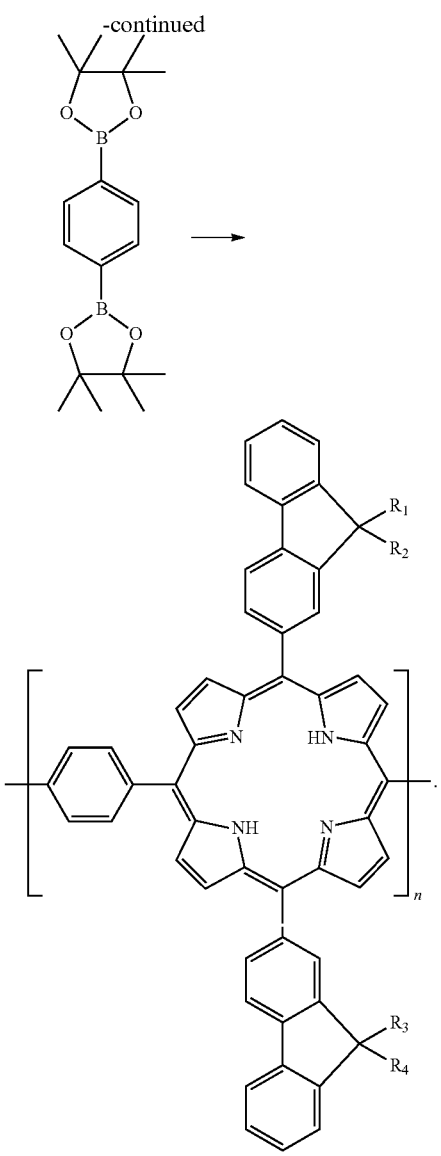

The specific procedure of step 3) is as follows. 1,4-bis(4,4,5,5-tetramethyl-1,3,2-dioxaborolanyl)benzene, 5,15-dibromo-10,20-bis(9,9-dialkylfluorenyl)porphyrin, and tetrakis(triphenylphosphine)palladium are added into a reaction container, wherein the ratio of the amount of the first two reactant may be 1/1, and the amount of tetrakis(triphenylphosphine)palladium, as a catalyst, may be about 0.1-20% of the molar amount the reactant. A certain amount of an aqueous solution of $Na_2CO_3$ and an organic solvent such as toluene are added to dissolve the reactants. The reaction container is then evacuated to remove oxygen, and charged with nitrogen. The solution is heated to 50-120° C. for 12-80 hours. After the reaction is completed, the product is purified as follows. The reaction product is poured into methanol. The precipitate is filtered with a Buchner funnel, and washed with diluted HCl. The solid is extracted with acetone in a Soxhelt extractor for 12-72 hours to remove the monomer and catalyst residues. The remaining polymer is dissolved in tetrahydrofuran and chloroform, to give the copolymer of the present embodiment. The value of n for the copolymer is preferably 5-50, more preferably 10-30. In the practice of the preparation, desired degree of polymerization may be achieved by selecting the organic solvent, and controlling the reaction temperature, the reaction time, the amount of the reactants, and the type and the amount of the catalyst.

In the first scheme in the method described above, the copolymer is directly synthesized from the three monomers, compounds A, B and 1,4-bis(dipyrrolylmethyl)benzene. The synthesis route is simple and mature, which is a one-step synthesis, thereby reduces the process steps and the production cost. In the second scheme, bromination reaction and Suzuki coupling reaction are both well-established reactions. Therefore, the synthesis route is also mature with low costs, high yields and mild conditions, and is easy to control. The two schemes both make it possible to increase the solubility and molecular weight of the product by introducing alkyl, and to achieve a polymer which enables spin coating.

The fluorenylporphyrin-benzene copolymer of the present embodiment may be used in various photoelectric or semiconductive devices, such as organic photo-electric materials, solar cell devices, organic field effect transistors, organic electroluminescent devices, organic optical storage devices, organic non-linear materials and organic laser devices, as an organic photo-electric material, wherein the organic photo-electric material comprises a fluorenylporphyrin-benzene copolymer described above, to be used as an electron-donor material or a photoelectric conversion material. In the followings, solar cell devices, organic field effect transistors and organic electroluminescent devices will be illustrated as examples. Other devices, such as organic optical storage devices, organic non-linear materials and organic laser devices are similar in that they use the fluorenylporphyrin-benzene copolymer of the present embodiment as the optical storage material, non-linear material, laser material, or semiconductive material therein.

Figure 3:
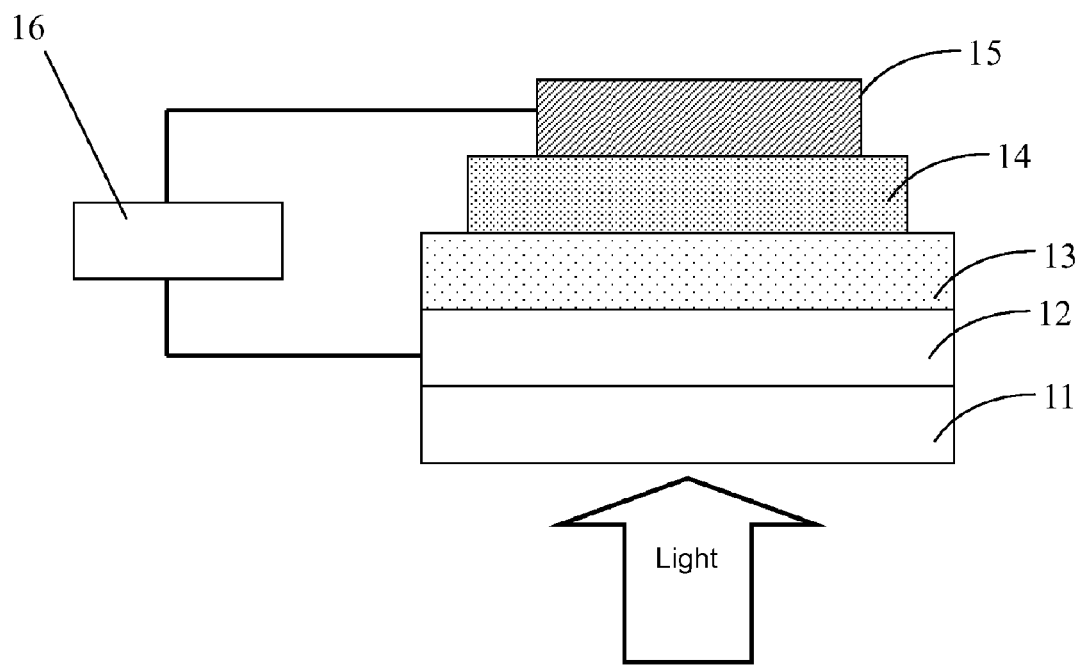
FIG. 3 is a structural scheme of a solar cell device comprising a fluorenylporphyrin-benzene copolymer in an embodiment of the present invention.

Refer to FIG. 3, which shows a solar cell device using the fluorenylporphyrin-benzene copolymer of the present embodiment, which comprises a glass substrate layer 11, a transparent anode 12, an intermediate auxiliary layer 13, an active layer 14, a cathode 15, which are stacked in sequence. The intermediate auxiliary layer 13 uses polyethylenedioxythiophene:polystyrene-sulfonate composite (PEDOT:PSS). The active layer 14 comprises an electron-donor material and an electron-acceptor material, in which the electron-donor material employs the fluorenylporphyrin-benzene copolymer described above, and the electron-acceptor material may be [6,6]phenyl-$C_{61}$-butyric acid methyl ester (PCBM). The transparent anode 12 may employ indium tin oxide (ITO), especially indium tin oxide with a sheet resistance of 10-20 Ω/sq. The cathode 15 may employ an aluminum electrode or a double metal-layer electrode, such as Ca/Al, Ba/Al or the like. The glass substrate layer 11 may be used as the bottom layer. In the manufacturing, an ITO glass is selected, sonicated, treated with oxygen-Plasma, and coated with an intermediate auxiliary layer 13. Then, the fluorenylporphyrin-benzene copolymer and the electron-acceptor material and blended and coated (e.g. spin coated) on the intermediate auxiliary layer 13 to form the active layer 14. Then, a cathode 15 is deposited on the active layer 14 by vacuum evaporation, to give the solar cell devices described above. In a preferred embodiment, the thicknesses of the transparent anode 12, the intermediate auxiliary layer 13, the active layer 14, and the double metal Ca and Al layers are 160 nm, 40 nm, 150 nm, 20 nm, 70 nm, respectively.

As shown in the figure, under light radiation, the light passes through the glass substrate layer 11 and the ITO electrode 12. The fluorenylporphyrin-benzene copolymer in the active layer 14 absorbs the light energy and produces excitons which immigrate to the interface of the electron-donor/acceptor material and transfer electrons to the acceptor material, e.g. PCBM to achieve the separation of the charges, and thereby forming free carriers, i.e. free electrons and holes. These free electrons are transported to the metal cathode along the acceptor material and collected by the cathode, whereas the free holes are transported to the ITO anode along the electron-donor material and collected by the anode, thereby forming photocurrent and photovoltage and achieving photoelectric conversion. When an external load 16 is connected, it can be powered. In this process, the fluorenylporphyrin-benzene copolymer, due to its broad spectral response range, may utilize the light energy more sufficiently, to achieve higher photoelectric conversion efficiency, and improve the ability of the solar cell devices to produce electric power. In addition, the mass of the solar cell devices may be lowered by using this kind of organic material. Moreover, by introducing alkyl, the manufacturing of the solar cell device may be conducted by spin coating or the like, which facilitates large-scale production.

Figure 4:
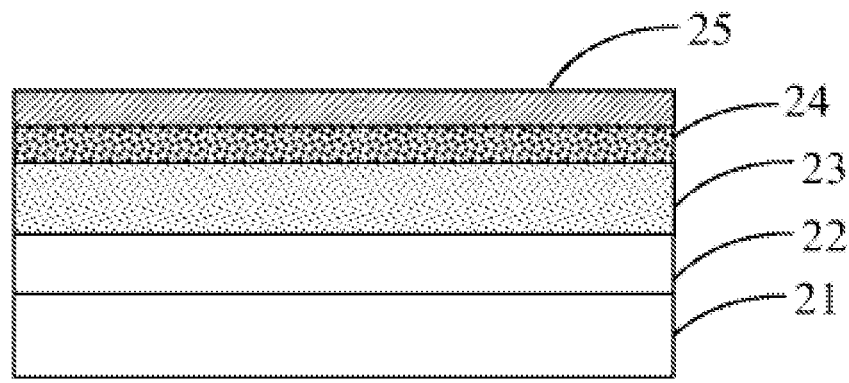
FIG. 4 is a structural scheme of an organic electroluminescent device comprising a fluorenylporphyrin-benzene copolymer in an embodiment of the present invention.

Refer to FIG. 4, which shows an organic electroluminescent device using the fluorenylporphyrin-benzene copolymer in the above embodiment, which comprises a glass substrate layer 21, a transparent anode 22, a luminous layer 23, a buffer layer 24 and a cathode 25, which are stacked in sequence. The transparent anode 22 may employ indium tin oxide (ITO), especially indium tin oxide with a sheet resistance of 10-20 Ω/sq. The luminous layer 23 comprises the fluorenylporphyrin-benzene copolymer in the above embodiment. The buffer layer 24 may employ LiF, but is not limited thereto. The cathode 25 may be, but not limited to, metal Al or Ba. Accordingly, in a specific embodiment, the structure of the organic electroluminescent devices is represented by: ITO/fluorenylporphyrin-benzene copolymer/LiF/Al. Each layer may be formed by currently used methods, and the fluorenylporphyrin-benzene copolymer may be formed on ITO by spin coating.

Figure 5:
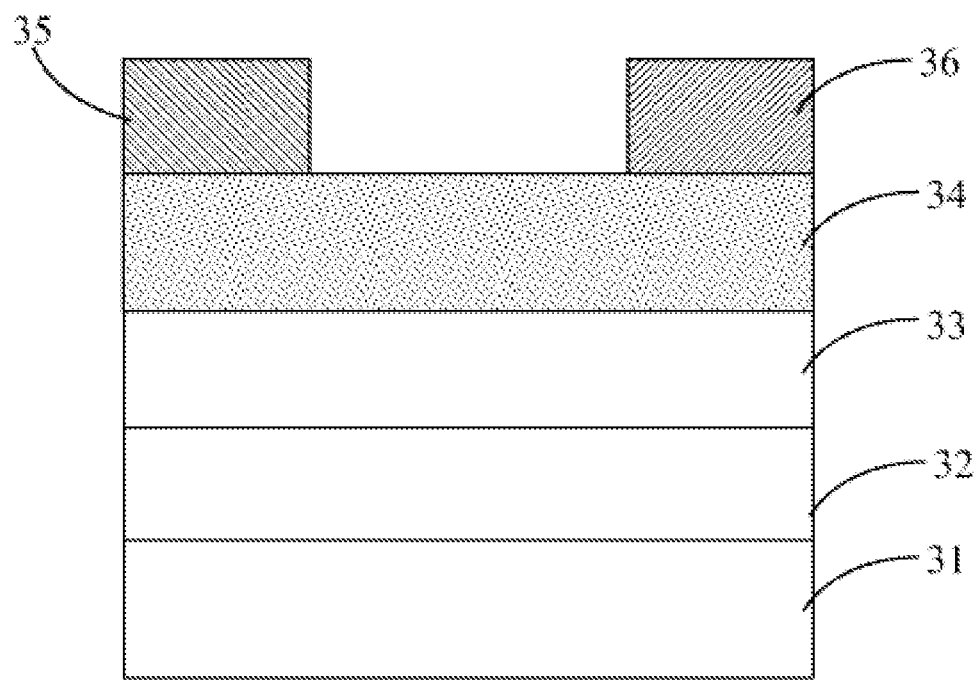
FIG. 5 is a structural scheme of an organic field effect transistor comprising a fluorenylporphyrin-benzene copolymer in an embodiment of the present invention.

Refer to FIG. 5, which shows an organic field effect transistor using the fluorenylporphyrin-benzene copolymer of the present embodiment, which comprises a substrate 31, an insulating layer 32, a modifying layer 33, an organic semiconductor layer 34 and a source electrode 35 and a drain electrode 36 disposed on the organic semi-conductor layer 34, which are stacked in sequence. The substrate 31 may be, but is not limited to, highly doped silicon chip (Si), and the insulating layer 32 may be, but is not limited to, $SiO_2$ with a thickness of micro- and nano-meter scales (e.g. 450 nm). The organic semi-conductor layer 34 employs the fluorenylporphyrin-benzene copolymer described above. The source electrode 35 and the drain electrode 36 may both be, but is not limited to, gold. The modifying layer 33 may be, but is not limited to, octadecyltrichlorosilane. The substrate 31, the insulating layer 32, the modifying layer 33 and the source electrode 35 and the drain electrode 36 may be formed by know processes. The organic semi-conductor layer 34 may be formed by spin coating the fluorenylporphyrin-benzene copolymer in the above embodiment on the insulating layer 32 modified by the modifying layer 33.

The method for preparing the fluorenylporphyrin-benzene copolymer and the properties thereof will be illustrated by referring to specific Examples. The compounds A, B and dipyrrolylmethane, 1,4-bis(dipyrrolylmethyl)benzene, 1,4-bis(4,4,5,5-tetramethyl-1,3,2-dioxaborolanyl)benzene used in the Examples may be prepared according to the methods described above, or may be commercially available, but are not limited thereto.

EXAMPLE 1

In Example 1, $R_1$, $R_2$, $R_3$, $R_4$ are all hexyl. Accordingly, the formula is shown below:

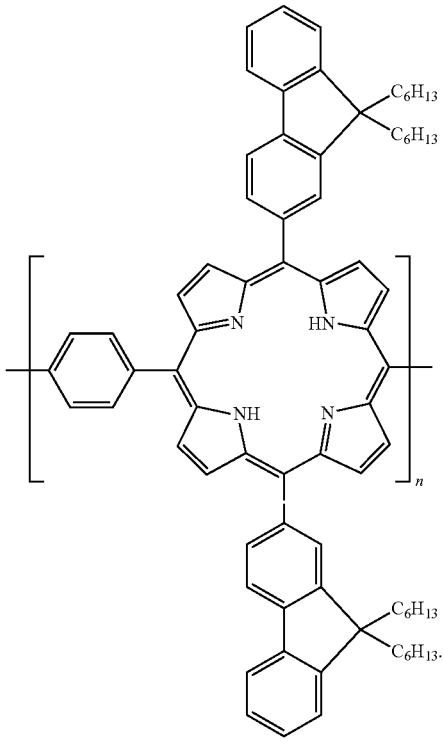

As can be seen from the formula, the fluorenylporphyrin-benzene copolymer of Example 1 has a symmetric difluorenyl structure. With this symmetric structure, the fluorenylporphyrin-benzene copolymer has good light-absorption performance, and photoelectric properties. The preparation of the fluorenylporphyrin-benzene copolymer of Example 1 follows the first scheme. As $R_1$, $R_2$, $R_3$, $R_4$ are all hexyl, compounds A and B are both 9,9-dihexyl-2-aldehyde fluorene. Accordingly, only one raw material is needed, which simplifies the preparation procedure and lowers the production costs. In addition, the yield is higher. If this symmetric structure is not used, the compounds A and B have different structures. Accordingly, different raw materials are needed, and more by-products would be resulted.

The specific procedure is as follows. 9,9-dihexyl-2-aldehyde fluorene and 1,4-bis(dipyrrolylmethyl)benzene (in a molar ratio of 2/1) are weighed into a reaction container and dissolved in dichloromethane. An appropriate amount of trifluoro acetic acid is added and stirred overnight (about 12-14 hours). Dichloro dicyano benzoquinone (two molar equivalents) is added, and further stirred. Triethylamine is added to quench the solution. Then the purification is conducted as follows. The reaction product is concentrated, and filtered. The solid is washed, and the filtrate is collected. Half of the solvents are evaporated. A methanol solution is added. The precipitation occurs after standing is filtered. The solid is collected, subjected to silica gel column chromatography separation, using petroleum ether/ethyl acetate as an eluent, and dried to give the product, i.e. the copolymer shown in the above formula.

EXAMPLE 2

In Example 2, $R_1$, $R_2$, $R_3$, $R_4$ are also hexyl. The difference is that the compound is prepared with the second scheme, and the specific procedure is as follows.

Step 1: Preparation of 5,15-bis(9,9-dihexylfluorenyl)porphyrin

The specific procedure is as follows. A moisture-free and oxygen-free system is set up. Compounds A, B and dipyrrolylmethane in a molar ratio of 1:1:2 are weighted. The compounds A and B have the same structure, which is 9,9-dihexyl-2-aldehyde fluorene. These compounds are dissolved in dichloromethane, and charged with nitrogen for 30 minutes. An appropriate trifluoro acetic acid is added with a syringe. The stirring is continued at room temperature for 3 hours, followed by adding two equivalents of dichloro dicyano benzoquinone, and stirring for further 30 minutes at room temperature. Triethylamine is then added to quench the reaction. Purification is conducted as follows: concentrating by removing the organic solvent, filtering, collecting the filtrate, removing the organic solvent by rotary evaporation, conducting flash silica gel column chromatographic separation eluted with dichloromethane, removing the organic solvent by rotary evaporation, and recrystallizing in ethyl ether/methanol to give the product.

Step 2: Preparation of 5,15-dibromo-10,20-bis(9,9-dihexylfluorenyl)porphyrin 5,15-bis(9,9-dihexylfluorenyl)porphyrin is dissolved in chloroform, followed by added a small amount of pyridine. The reaction mixture is cooled to 0° C., followed by adding an appropriate amount of N-bromosuccinimide. After stirring for 0.5 hours, the mixture is warmed up to room temperature, and stirred for further 4 hours. Acetone is added to terminate the reaction. The organic solvents are removed and the residue is recrystallized in ethyl ether/methanol to give the product.

Step 3: Preparation of the Fluorenylporphyrin-Benzene Copolymer

The specific procedure is as follows. 1.0 mmol 1,4-bis(4,4,5,5-tetramethyl-1,3,2-dioxaborolanyl)anthracene, 1.0 mmol 5,15-dibromo-10,20-bis(9,9-dialkylfluorenyl)porphyrin, 0.01 mmol tetrakis(triphenylphosphine)palladium, 3 ml $Na_2CO_3$ aqueous solution (2 mol/L) and 20 ml toluene solvent are added into a round-bottom flask. The reaction flask is then evacuated to remove oxygen, and charged with nitrogen. The solution is refluxed in a $N_2$ atmosphere for 48 hours to carry out the reaction. After the reaction is completed, the product is purified as follows. The reaction product is poured into methanol. The precipitate is filtered with a Buchner funnel, and washed with diluted HCl. The solid is washed with acetone in a Soxhelt extractor for 12-72 hours to remove the monomer and catalyst residues. The remaining polymer is dissolved in tetrahydrofuran and chloroform, and the yield is about 30-51%.

In the above fluorenylporphyrin-benzene copolymer, the fluorenyl or derivatives thereof have superior photo- and thermal stabilities and film-forming properties, and its structure is easy to be modified. By introducing a benzene ring into the above copolymer, the electron cloud density of the skeleton of the polymer is increased, thereby making the band gap of the fluorenyl copolymer narrower, and the spectral response range broader. The porphyrin structure makes the copolymer to have higher quantum efficiency in charge transfer and energy transfer, good electron buffering property and optical, electrical and magnetic properties, good stiffness and softness, good thermal stability and environmental stability. When the above fluorenylporphyrin-benzene copolymer is used in organic photo-electric materials, solar cell devices, organic field effect transistors, organic electroluminescent devices, organic optical storage devices, organic non-linear materials or organic laser devices, it can improve their photoelectric or semi-conductor-related properties, and lower the weight of the devices, and facilitate their mass production.

The examples described above are only preferred embodiments of the present invention, and are not intended to limit the present invention. Any amendment, equivalent substitution and improvement within the spirit and principle of the present invention fall within the scope of the present invention.

We claim:

1. A fluorenylporphyrin-benzene copolymer, comprising a copolymer represented by formula (1):

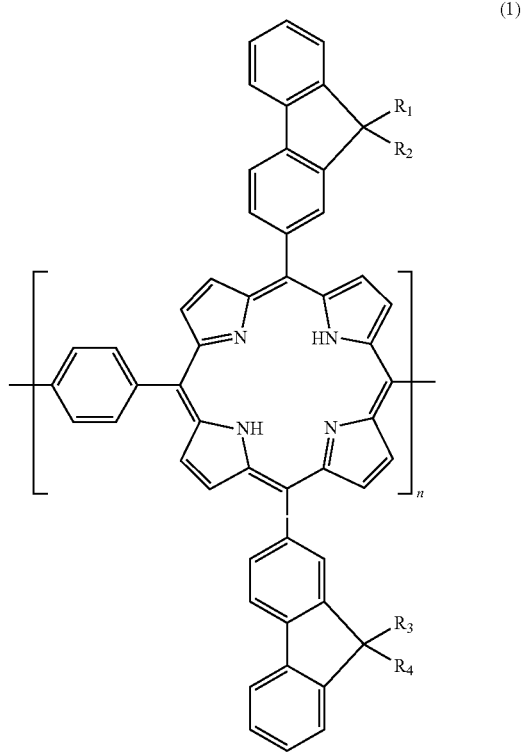

(1)

wherein, $R_1$, $R_2$, $R_3$, $R_4$ are the same or different from each other and are $C_1$-$C_{16}$ alkyl; and n is an integer of 1-100.

2. The fluorenylporphyrin-benzene copolymer according to claim 1, wherein $R_1$, $R_3$ are the same $C_1$-$C_{16}$ alkyl, and $R_2$, $R_4$ are the same $C_1$-$C_{16}$ alkyl.

3. The fluorenylporphyrin-benzene copolymer according to claim 1, wherein $R_1$, $R_2$, $R_3$, $R_4$ are the same $C_1$-$C_{16}$ alkyl.

4. The fluorenylporphyrin-benzene copolymer according to claim 1, wherein n is an integer of 5-50.

5. A method for preparing a fluorenylporphyrin-benzene copolymer, comprising the steps of:

providing compounds A and B represented by the following formulae, respectively, and dipyrrolylmethane or 1,4-bis(dipyrrolylmethyl)benzene,

A:

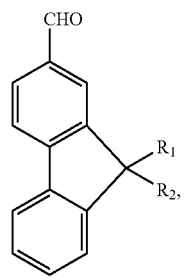

-continued

B:

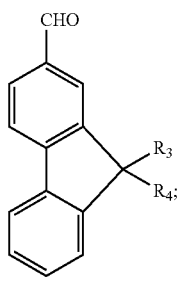

wherein $R_1$, $R_2$, $R_3$, $R_4$ are the same or different from each other and are $C_1$-$C_{16}$ alkyl;
conducting a polycondensation/oxidation reaction of compounds A, B with 1,4-bis(dipyrrolylmethyl)benzene in a system containing a catalyst, an oxidant and an organic solvent, to give the compound represented by formula (1); or conducting a polycondensation/oxidation reaction of compounds A, B with dipyrrolylmethane in a system containing a catalyst, an oxidant and an organic solvent, and conducting a bromination reaction of the product, and conducting a Suzuki coupling reaction of the brominated product with 1,4-bis(4,4,5,5-tetramethyl-1,3,2-dioxaborolanyl)benzene, to give the copolymer represented by formula (1):

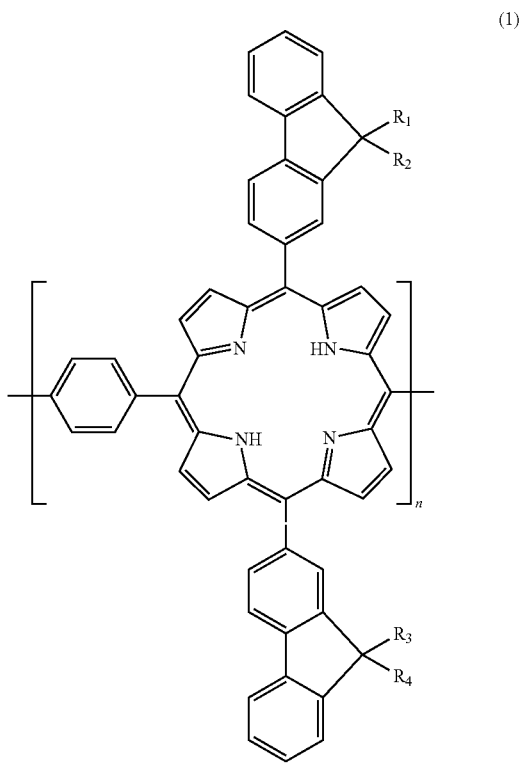

(1)

wherein n in formula (1) is an integer of 1-100.

6. The method for preparing the fluorenylporphyrin-benzene copolymer according to claim 5, wherein the polycondensation/oxidation reaction comprises: selecting compounds A, B and dipyrrolylmethane or 1,4bis(dipyrrolylmethyl)benzene, dissolving in an organic solvent, adding trifluoro acetic acid as a catalyst, stirring for 12-14 hours, adding dichloro dicyano benzoquinone as an oxidant, continuing stirring, adding triethylamine to quench the reaction, and purifying to obtain the product.

7. The method for preparing the fluorenylporphyrin-benzene copolymer according to claim 5, wherein the Suzuki coupling reaction comprises: selecting 1,4-bis(4,4,5,5-tetramethyl-1,3,2-dioxaborolanyl)benzene, 5,15-dibromo-10,20-bis(9,9-dialkylfluorenyl)porphyrin, and an organic palladium catalyst, adding an alkali solution and an organic solvent to dissolve the reactants, evacuating to remove oxygen and charging with nitrogen, and heating the solution to 50-120° C. for 12-80 hours, to obtain the fluorenylporphyrin-benzene copolymer.

8. The method for preparing the fluorenylporphyrin-benzene copolymer according to claim 5, wherein the bromination reaction comprises: dissolving the product of the polycondensation/oxidation reaction in an organic solvent, adding pyridine, a pyridine derivative, or triethylamine as a catalyst, cooling the reaction mixture to 0° C., adding N-bromosuccinimide, stirring, warming back to room temperature, stirring for further several hours, adding acetone to terminate the reaction, removing solvents, and recrystallizing in ethyl ether/methanol, to obtain the brominated product.

9. The method for preparing the fluorenylporphyrin-benzene copolymer according to claim 5, wherein the Suzuki coupling reaction is followed by the following purification procedure: pouring the product of the Suzuki coupling reaction into methanol, filtering to separate the precipitate, washing, and extracting the obtained solid with acetone in a Soxhelt extractor to remove the monomer and catalyst residues, to obtain the fluorenylporphyrin-benzene copolymer.

10. A material comprising the fluorenylporphyrin-benzene copolymer according to claim 1, wherein the material is selected from organic photo-electric materials and organic non-linear materials.

11. A device comprising the fluorenylporphyrin-benzene copolymer according to claim 1, wherein the device is selected from solar cell devices, organic field effect transistors, organic electroluminescent devices, organic optical storage devices, and organic laser devices.

\* \* \* \* \*